US010322000B2

(12) United States Patent
Orth et al.

(10) Patent No.: US 10,322,000 B2
(45) Date of Patent: Jun. 18, 2019

(54) SIZING CATHETERS, METHODS OF SIZING COMPLEX ANATOMIES AND METHODS OF SELECTING A PROSTHESIS FOR IMPLANTATION

(71) Applicant: Medtronic Vascular, Inc., Santa Rosa, CA (US)

(72) Inventors: Geoffrey Orth, Santa Rosa, CA (US); Mostafa Toloui, Santa Rosa, CA (US); Kshitija Garde, Santa Rosa, CA (US); Michael Krivoruchko, Santa Rosa, CA (US); Brian McHenry, Santa Rosa, CA (US); Wei Wang, Santa Rosa, CA (US); Tracey Tien, Santa Rosa, CA (US); Sarah Ahlberg, Santa Rosa, CA (US); Cynthia Clague, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 15/946,043

(22) Filed: Apr. 5, 2018

(65) Prior Publication Data

US 2018/0289488 A1  Oct. 11, 2018

Related U.S. Application Data

(60) Provisional application No. 62/481,853, filed on Apr. 5, 2017.

(51) Int. Cl.
*A61F 2/24* (2006.01)
*A61B 5/00* (2006.01)
(Continued)

(52) U.S. Cl.
CPC .......... *A61F 2/2496* (2013.01); *A61B 5/1076* (2013.01); *A61B 5/6853* (2013.01); *A61B 5/02007* (2013.01); *A61F 2/2427* (2013.01)

(58) Field of Classification Search
CPC . A61B 5/1076; A61B 5/6853; A61B 5/02007; A61F 2/2496; A61F 2/2427
See application file for complete search history.

(56) References Cited

U.S. PATENT DOCUMENTS 7,454,244 B2  11/2008  Kassab et al.
7,818,053 B2  10/2010  Kassab
(Continued)

FOREIGN PATENT DOCUMENTS

WO         2014120508 A1   8/2014
WO    WO 2014 179775 A1  11/2014

OTHER PUBLICATIONS

PCT communication dated Feb. 7, 2018 in corresponding PCT Appln.No. PCT/US2018/026274.

*Primary Examiner* — Edward Park

(57) ABSTRACT

Aspects of the disclosure include sizing catheters and methods for determining the size and other physical parameters of an internal orifice or lumen. Embodiments include a sizing catheter assembly having a handle assembly and a catheter assembly including at least one catheter extending from the handle assembly. The catheter assembly also includes at least two sizers, which can be adjustably spaced from each other. Each of the sizers are configured to conform to respective portions of a lumen of a patient's anatomy. The sizing catheter is configured such that the sizers are configured to specify or determine first and second dimensions of the lumen and also distance between the sizers. The sizers can include valve leaflets or the sizing catheter can include a temporary valve. Additional aspects include software/methods of assessing and determining an appropriate implantable device that can include assessing the biomechanical interaction between the device and the anatomy.

20 Claims, 15 Drawing Sheets

A-P Cranial View

Left Lateral View

(51) Int. Cl.
*A61B 5/107* (2006.01)
*A61B 5/02* (2006.01)

(56) References Cited

U.S. PATENT DOCUMENTS

| | | |
|---|---|---|
| 8,078,274 B2 | 12/2011 | Kassab |
| 8,486,014 B2 | 7/2013 | Kelly et al. |
| 2006/0259137 A1 | 11/2006 | Artof et al. |
| 2008/0009746 A1 | 1/2008 | Forster et al. |
| 2011/0098602 A1 | 4/2011 | Campbell et al. |
| 2011/0245859 A1 | 10/2011 | Klaiman et al. |
| 2013/0123694 A1 | 5/2013 | Subramaniyan |
| 2013/0172989 A1 | 7/2013 | Campbell |
| 2014/0107768 A1 | 4/2014 | Venkatasubramanian |
| 2014/0275986 A1* | 9/2014 | Vertikov ................ A61B 5/061 600/424 |
| 2015/0339847 A1* | 11/2015 | Benishti ................ G16H 50/30 382/131 |
| 2016/0157798 A1* | 6/2016 | Anderson ............ A61B 5/743 600/427 |

* cited by examiner

SIZING CATHETERS, METHODS OF SIZING COMPLEX ANATOMIES AND METHODS OF SELECTING A PROSTHESIS FOR IMPLANTATION

CROSS-REFERENCE TO RELATED APPLICATIONS

This Non-Provisional Patent Application claims the benefit of the filing date of U.S. Provisional Patent Application Ser. No. 62/481,853, filed Apr. 5, 2017, the entire teachings of which are incorporated herein by reference.

BACKGROUND

The present disclosure relates to sizing catheters for determining the size and other physical parameters of an internal orifice or lumen, such as an artery, vein, pulmonary trunk or aorta, to provide a physician with information relating to size and/or other parameters of the internal lumen for use in selecting an appropriate prosthetic device, such as a prosthetic heart valve.

It is important to select an appropriately configured prosthetic heart valve because if the prosthetic heart valve does not fit properly, the prosthetic heart valve may migrate, leak or cause other problems. In order to select an appropriately sized prosthetic heart valve, the size, shape, topography, compliance and other physical parameters of a vessel lumen are often assessed. In some circumstances, an exhaustive image collection and image measurements are required to be analyzed for selecting a stented prosthetic heart valve configured to fit a patient's particular anatomy. Obtaining such images via a magnetic resonance angiogram (MRA) or computed tomography (CT scan) or the like requires a substantial amount of time and expense.

Various devices are also available for internally determining the size and other physical parameters of an internal orifice or lumen. Such devices can include an expandable member, such as a balloon, capable of expanding to contact tissue and collect information relating to physical parameters of the tissue proximate the expandable member.

The present disclosure addresses problems and limitations associated with the related art.

SUMMARY

As indicated above, it is important to select an appropriately configured prosthetic heart valve because if the prosthetic heart valve does not fit properly, it may migrate, leak or cause other problems. In order to select an appropriately sized prosthetic heart valve, the size, shape, topography, compliance and other physical parameters of a vessel lumen are assessed. Certain expandable members, such as balloons, used for conducting such an assessment of a patient's anatomy have their drawbacks. For example, it has been observed by the present inventors that balloons, for example, straighten out and deform to the anatomy as they are expanded. An additional drawback is that balloons block the flow of blood, which can cause patients distress and can alter physiologic function, which provides inaccurate results. Aspects of the disclosure address these limitations.

Certain disclosed embodiments include a sizing catheter assembly having a handle assembly and a catheter assembly extending from the handle assembly. The sizing catheter is arranged and configured for transluminal access by well-known techniques for assessing a patient's vasculature from an artery or vein, for example. The catheter assembly includes at least one catheter as well as a distal sizer positioned on a distal end of the catheter and a proximal sizer positioned on the catheter and adjustably spaced from the distal sizer. Each of the distal and proximal sizers are configured to deploy to conform to respective portions of a lumen of a patient's anatomy, such as a pulmonary trunk, for example. The sizing catheter is configured to determine first and second dimensions of the lumen at a selected distance between the distal and proximal sizers. The proximal and distal sizers can take a variety of forms. Optionally, one or more of the proximal and distal sizers can include a valve structure. Moreover, the sizing catheter can optionally include a temporary prosthetic valve positioned on the catheter.

Aspects of the disclosure also include methods of sizing a lumen of a patient's anatomy for selecting an appropriately sized prosthesis. Methods can include providing a sizing catheter, delivering the sizing catheter to a target site within the lumen; and determining dimensions of the lumen with the distal and proximal sizers including a diameter of the lumen proximate the distal and proximal sizers and also determining a distance between the distal and proximal sizers. Based on information obtained from the sizing catheter, the method can include selecting a prosthetic valve based on the sensed or measured dimensions and/or other sensed or measured lumen properties. Once the appropriate prosthetic valve is selected, the prosthetic valve can be delivered and deployed with an appropriate delivery device.

Additional aspects of the disclosure include methods and software for: 1) automatic patient screening; and/or 2) pre-operative planning of a stented prosthesis. In such methods, images of the anatomy and/or anatomy size measurements are made available or otherwise inputted to the software for modeling and automatic virtual device fit testing of one or more potential prosthetic devices. Anatomy size measurements can be obtained with any of the disclosed sizing catheter assemblies, for example. In various embodiments, the software includes a biomechanical interaction module that is programmed to predict and evaluate the biomechanical interaction between the device and the host anatomy.

Although much of the present disclosure is in relation to applications directed toward heart valve assessment. It will be understood, in view of the disclosure, that the disclosed embodiments can be adapted and applied for use in other vessel lumens and orifices of the human body.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1A:
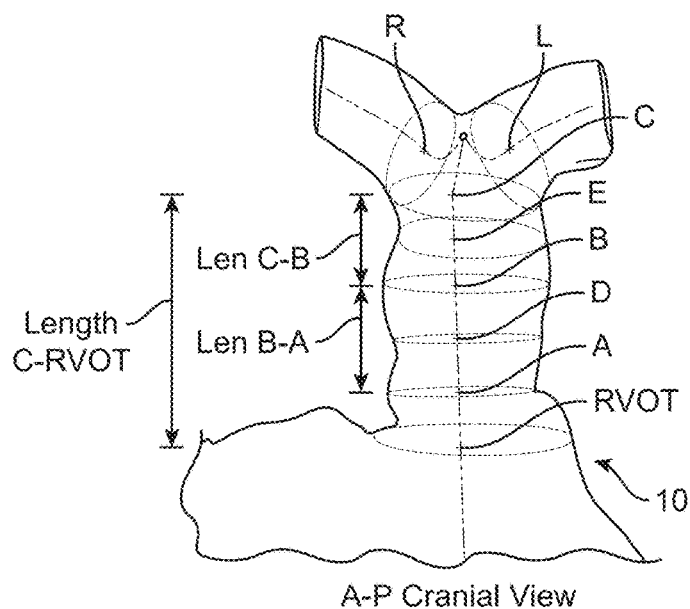
FIG. 1A is an antero-posterior/cranial view of a pulmonary trunk.
Figure 1B:
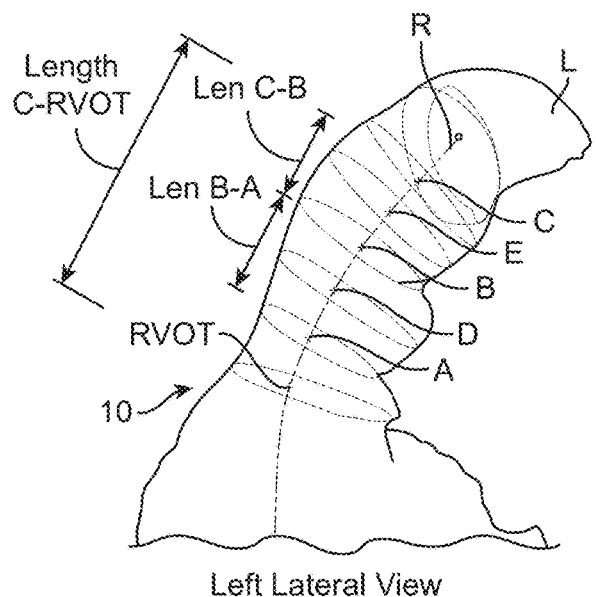
FIG. 1B is a left lateral view of the pulmonary trunk of FIG. 1A.

The sizing of a bodily orifice in which a prosthetic device (e.g., a transcatheter prosthetic heart valve) is to be implanted is typically desired. A properly sized prosthetic heart valve is important to prevent migration of the prosthetic heart valve or embolization, prevent paravalvular leakage, prevent excessive hemodynamic loads from poor apposition, prevent compression on leaflets of the prosthetic heart valve and also to prevent tissue erosion, for example. Some sizing procedure embodiments require a collection of images and/or image measurements to determine an appropriate prosthetic heart valve suitable to fit the patient's anatomy. FIGS. 1A-1B include example images of a pulmonary trunk 10 and illustrate various measurements that can be obtained to assess useful physical parameters of the anatomy. For example, useful measurements can include cross-sectional measurements such as diameter or perimeter at a sub-valve A, supra-valve B, pre-bifurcation C, mid-valve D between A and B, mid-trunk E between B and C and also at the right ventricular outflow tract RVOT, for example. In addition, obtaining length measurements can also be beneficial including an overall MPA length C-RVOT, sub-valve A to supra valve length B and supra-valve B to pre-bifurcation length C, for example.

Figure 2:
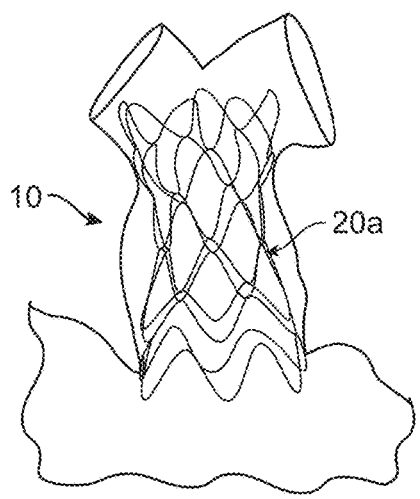
FIG. 2 is a partially transparent view of a stented prosthesis deployed within the pulmonary trunk of FIGS. 1A-1B.
Figure 3:
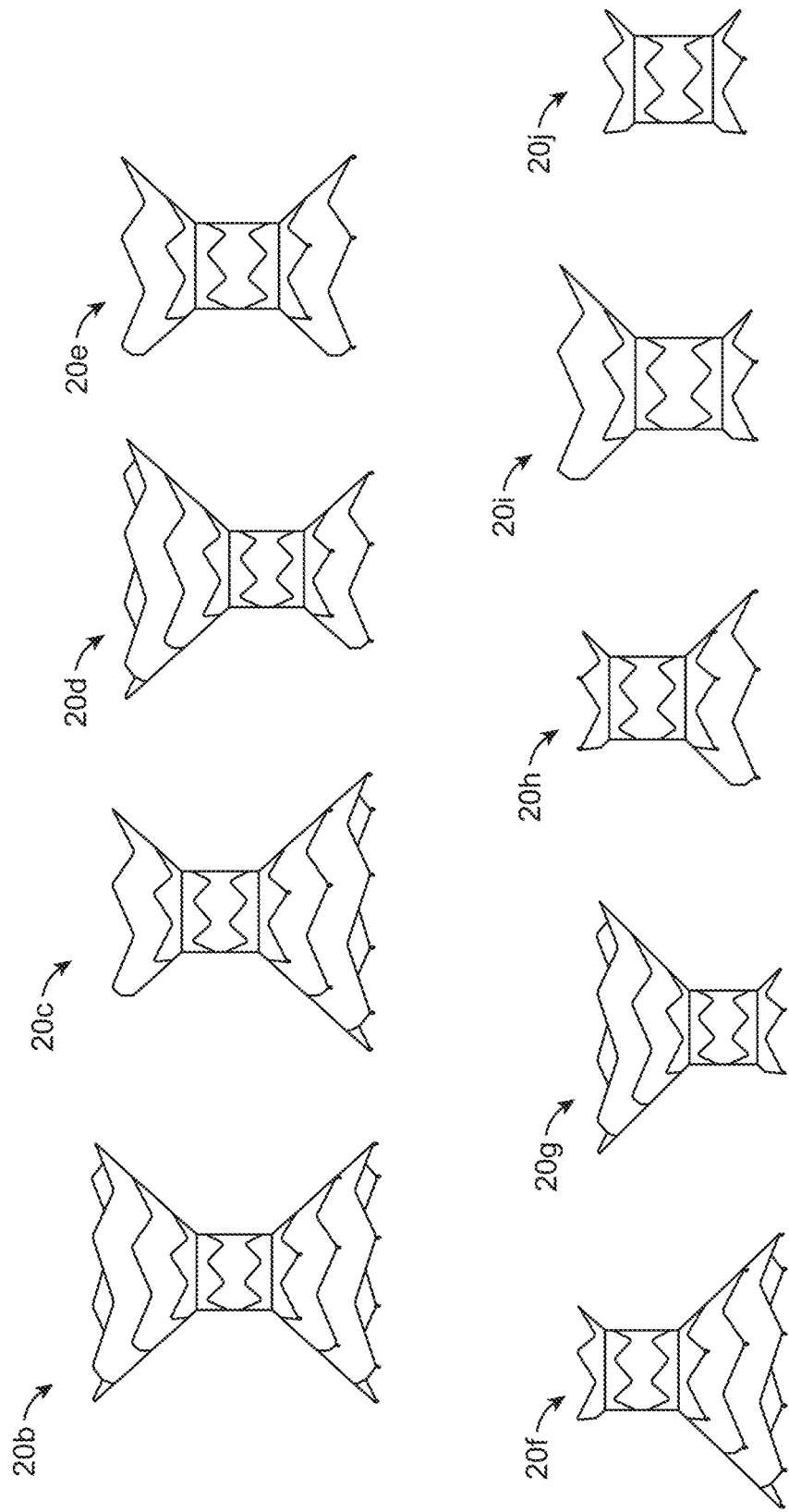
FIG. 3 schematically illustrates a plurality of stented prostheses having a variety of configurations.

After obtaining measurements regarding parameters of the anatomy of interest, an appropriate prosthetic heart valve can be selected such that the prosthetic heart valve provides adequate outward force, stability and sealing when implanted. In addition, the prosthetic heart valve can be selected to have various inflow and outflow end lengths and shapes, as appropriate, to suit the particular characteristics of the anatomy. See, for example, FIG. 2, which illustrates a stented prosthetic heart valve 20a, which is adequately configured and implanted within the particular pulmonary trunk 10. See also, FIG. 3, which illustrates additional non-limiting examples of other prosthetic heart valves 20b-j having different configurations suitable for different anatomical variations.

As indicated herein, stented prostheses may assume a wide variety of configurations. Stented prostheses can include, for example, stented prosthetic heart valves ("prosthetic valves"), such as a bioprosthetic heart valve having tissue leaflets or a synthetic heart valve having polymeric, metallic or tissue-engineered leaflets, and can be specifically configured for replacing valves of the human heart. The stented prostheses of the present disclosure may be self-expandable, balloon expandable and/or mechanically expandable or combinations thereof. In general terms, the prosthetic valves of the present disclosure include a stent or stent frame having an internal lumen maintaining a valve structure (tissue or synthetic), with the stent frame having a normal, expanded condition or arrangement and collapsible to a compressed condition or arrangement for loading within a transcatheter prosthetic valve delivery device. For example, the stents or stent frames are support structures that comprise a number of struts or wire segments arranged relative to each other to provide a desired compressibility and strength to the prosthetic valve. The struts or wire segments are arranged such that they are capable of self-transitioning from, or being forced from, a compressed or collapsed arrangement to a normal, radially expanded arrangement. The struts or wire segments can be formed from a shape memory material, such as a nickel titanium alloy (e.g., nitinol). The stent frame can be laser-cut from a single piece of material, or can be assembled from a number of discrete components.

Figure 4A:
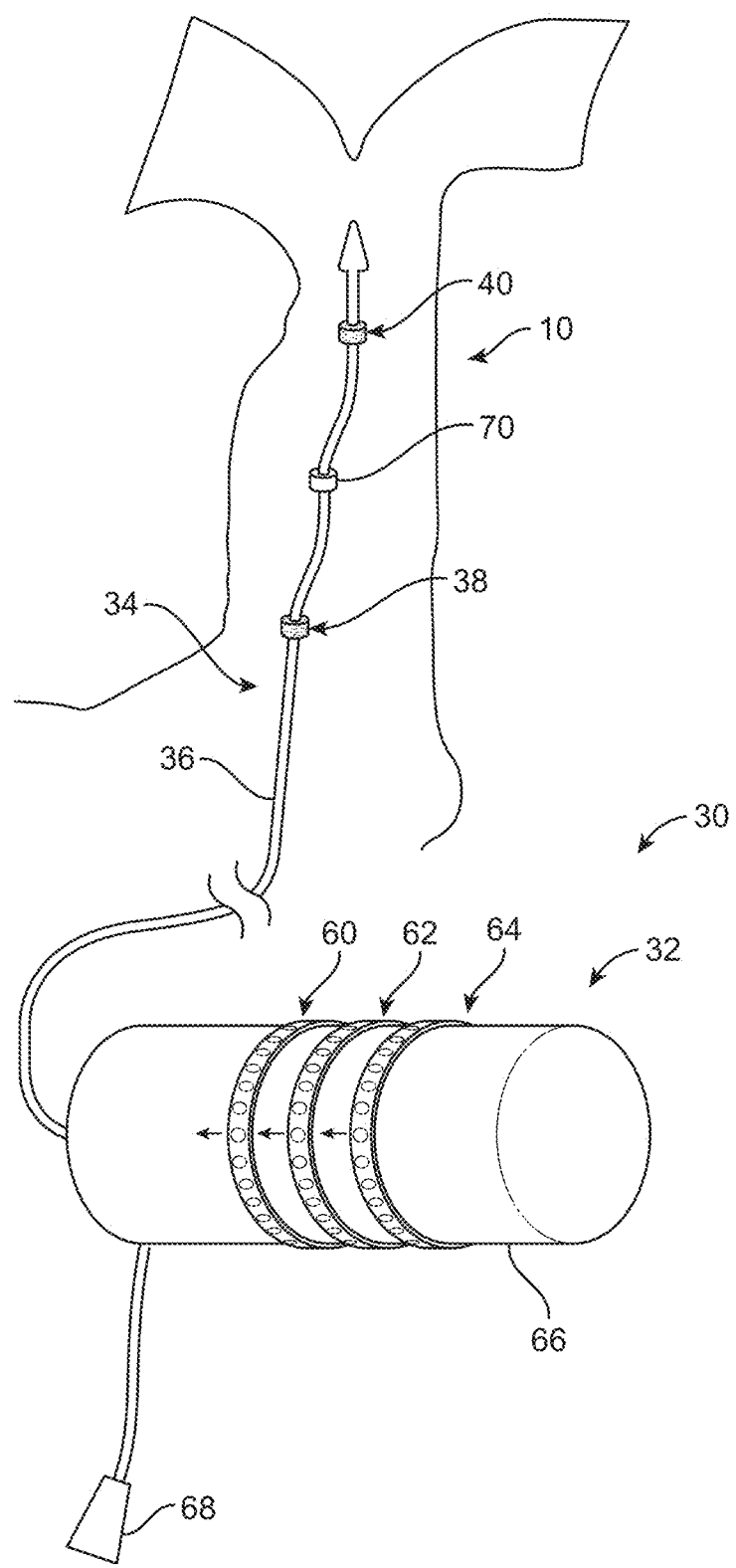
FIG. 4A is a schematic illustration of a sizing catheter having a proximal sizer, distal sizer and temporary valve in a delivery configuration positioned within the pulmonary trunk.
Figure 4B:
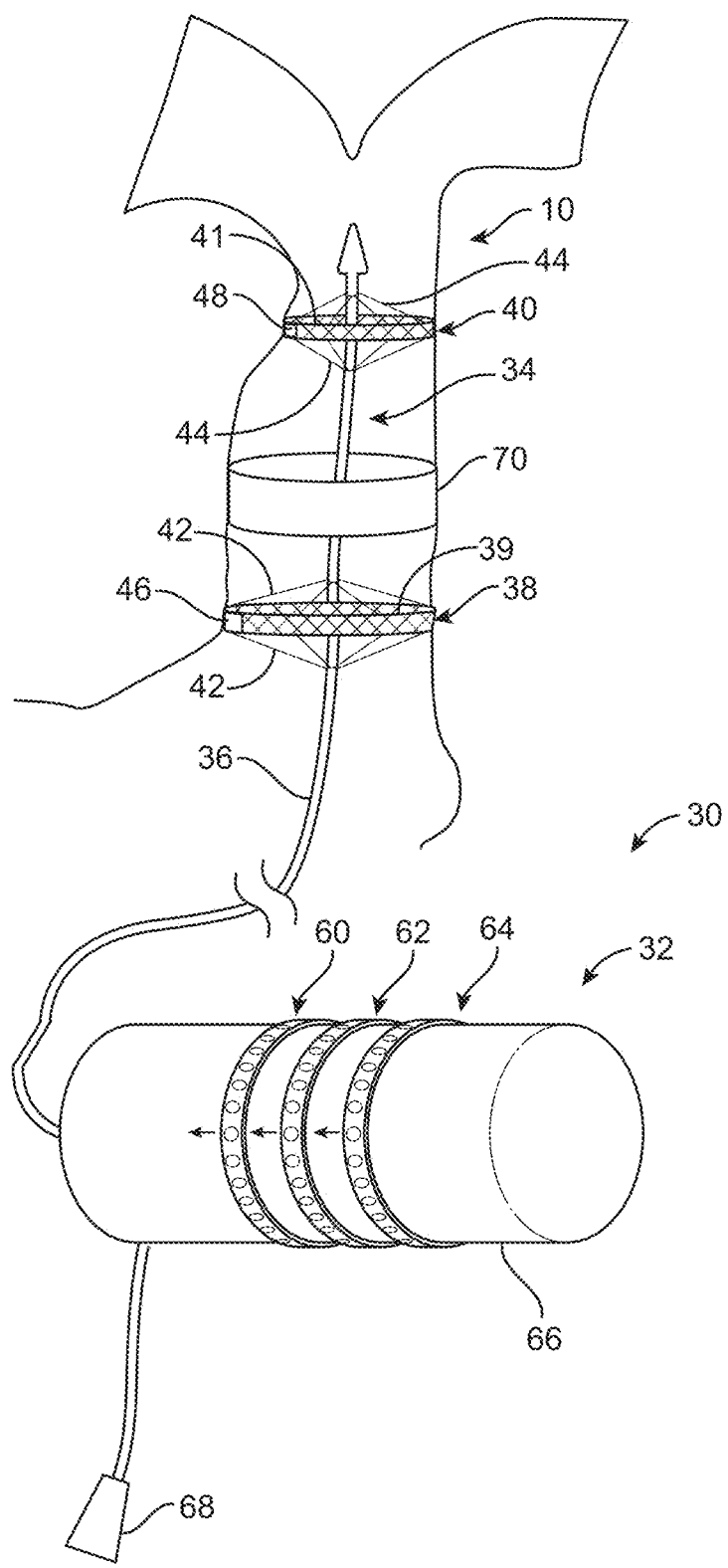
FIG. 4B is a schematic illustration of the sizing catheter of FIG. 4A; wherein the proximal sizer, the distal sizer and the temporary valve are in a deployed configuration positioned within the pulmonary trunk.

A schematic illustration of one sizing catheter device or "lumen sizing device" 30 that can be used to determine size and/or other shape parameters of a bodily lumen (e.g., the pulmonary trunk 10) is illustrated in FIGS. 4A-4B. The sizing catheter device 30 is arranged and configured for transluminal access by well-known techniques for assessing a patient's vasculature from a femoral vein or artery, for example. In one embodiment, the catheter assembly 30 is configured to be tracked over a previously inserted guide wire (not shown) for delivery to the target site 10. The sizing catheter device 30 includes a handle assembly 32 interconnected to a catheter assembly 34. The catheter assembly 34 includes one or more catheters 36 supporting proximal and distal sizers 38, 40, which are spaced apart along a length of the one or more catheters 36. In alternate embodiments, additional sizers can be provided (e.g., five sizers, ten sizers or more). In some embodiments, the most proximal and most distal sizers 38, 40 are spaced approximately 5 to 100 mm apart. In some embodiments, the most proximal and most distal sizers 38, 40 are spaced about 25 to about 55 mm apart. The spacing between the most proximal and most distal sizers 38, 40 might correspond to the length of the prosthetic heart valve that is intended to be implanted. In some embodiments, the sizers 38, 40 are connected to the catheter assembly 34 with one or more flexible elongate members 42, 44 extending to and controlled via the handle assembly 32 or the like to deploy the respective sizer 38, 40 (flexible elongate members 42 are generally referenced, see, FIG. 4B). Each sizer 38, 40 is arranged and configured to determine dimensions of the bodily lumen 10 in which the sizer 38, 40 is inserted. Therefore, in some embodiments, each sizer 38, 40 includes a flexible ring 39, 41 on which one or more sensors 46, 48 (generally referenced in FIG. 4B) positioned on or about the respective sizer 38, 40. In some embodiments, the sizers 38, 40 are further configured to determine the distance between the proximal and distal sizers 38, 40. Alternatively, the distance between the sizers 38, 40 is adjustable via the handle assembly 32 so that the distance between the sizers 38, 40 is determinable or known based on a user selected distance. For example, the distal sizer can be secured to a first catheter positioned within a second catheter (see also, FIGS. 7A-7D) and the handle assembly can be configured to change the position of the first catheter with respect to the second catheter, thus adjusting the position of the distal sizer with respect to the proximal sizer.

The sensors 46, 48 can be configured to obtain information regarding properties and characteristics of the lumen 10 that can be useful in determining an appropriately sized prosthetic heart valve or other prosthesis. In one non-limiting example, the sensors 46, 48 can include multiple electrodes positioned around the respective ring 39, 41 that are configured to measure the impedance between electrodes to determine when the sizer 38, 40 is positioned against tissue defining the lumen 10. For example, if the ring 39, 41 has a diameter such that it is surrounded by blood flow and not against tissue defining the lumen 10, an impedance measurement obtained by the electrodes may be low and when the electrodes of the sizer 38, 40 are in firm contact with tissue defining the lumen 10, the impedance measurement obtained by the electrodes may be higher. In this way, the diameter of the ring 39, 41 can be expanded until the ring 39, 41 is against tissue defining the lumen 10, thus indicating a diameter of the lumen 10 at that location. The sensors 46, 48 can also be configured to provide position-indicating information to assist a mapping process for determining the topography of the lumen 10. In further example embodiments, the sensors 46, 48 can include piezoelectric sensors, optical sensors, electromagnetic sensors, capacitive sensors and the like. The disclosed embodiments are not intended to be limited to the use of any particular sensor as there are many types of sensors that can suitably obtain useful information regarding a lumen.

The handle assembly 32 can be of a variety of configurations suitable for directing the catheter assembly 34 through a bodily lumen, such as through a femoral vein to a pulmonary artery or the like. The handle assembly 32 can further be configured to transition the sizers 38, 40 from a delivery position (FIG. 4A) in which the rings 39, 41 are compressed or unexpanded for ease of delivery, into a deployed position (FIG. 4B), in which the rings 39, 41 are expanded to contact tissue of the lumen to be sized. In one example embodiment, a first control 60 is configured and arranged to adjust and indicate the expansion or perimeter of the distal ring 41, a second control 62 is configured and arranged to adjust and indicate the distance between the proximal and distal sizer 38, 40 and a third control 64 is configured and arranged to indicate and adjust the expansion or perimeter of the proximal ring 39. The controls 60-64 may be configured to be actuated by advancing the respective control 60-64 with respect to a body 66 of the handle assembly 32. In this way, all controls 60-64 can be operated independently of one another. The handle assembly 32 can include one or more ports 68 interconnected for the injection of contrast material and/or for connection to one or more inflation sources (not shown) to inflate a temporary valve, the sizer 38 and/or the sizer 40 as will be discussed in detail below.

Optionally, the sizing catheter 30 can further include a temporary prosthetic valve 70 (schematically shown). In some embodiments, the temporary prosthetic valve 70 is positioned on the catheter assembly 34 between the proximal and distal sizers 38, 40. In other alternate embodiments (not shown), either the proximal sizer or the distal sizer 38, 40 can include a valve structure including valve leaflets (similar or identical to the structure of 70 shown in greater detail in FIGS. 5A-5D) so that when in the deployed, expanded position, the respective sizer 38, 40 functions also as a temporary prosthetic valve. In this way, the valve structure would be provided within one respecting ring 39, 41.

Figure 5A:
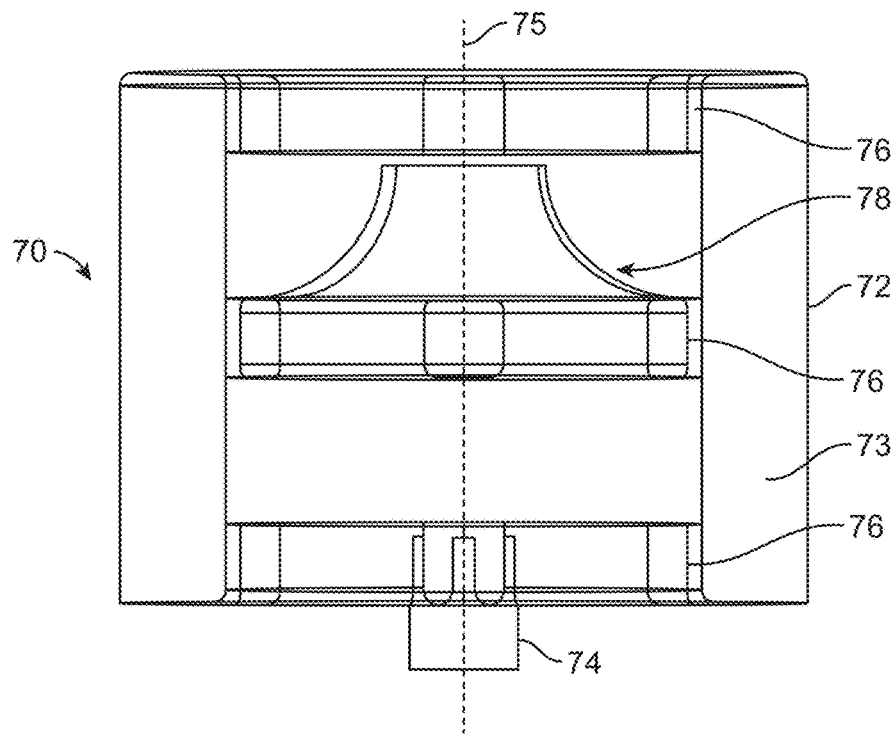
FIG. 5A is a partially transparent side view of the temporary valve of FIGS. 4A-4B.
Figure 5B:
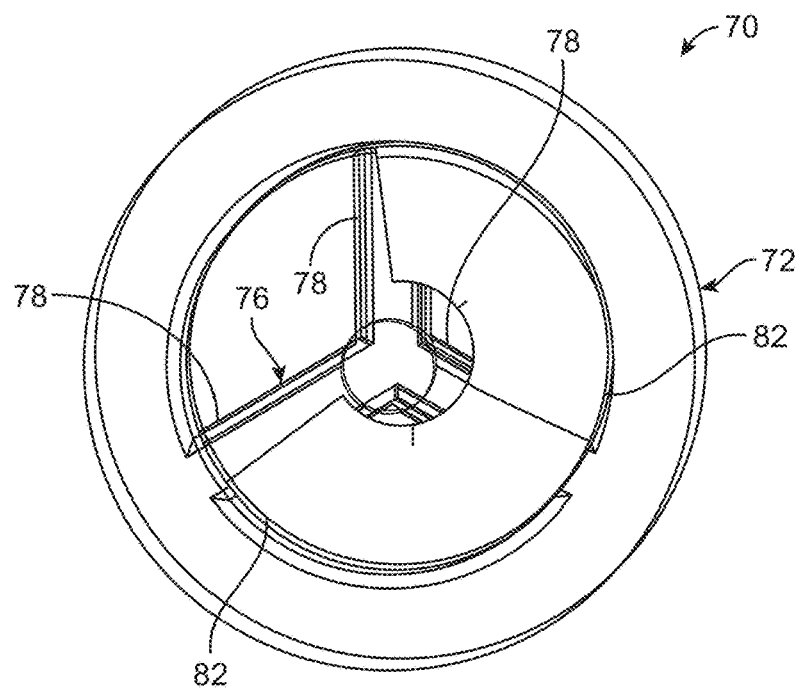
FIG. 5B is a partial, top view of the temporary valve of FIG. 5A.
Figure 5C:
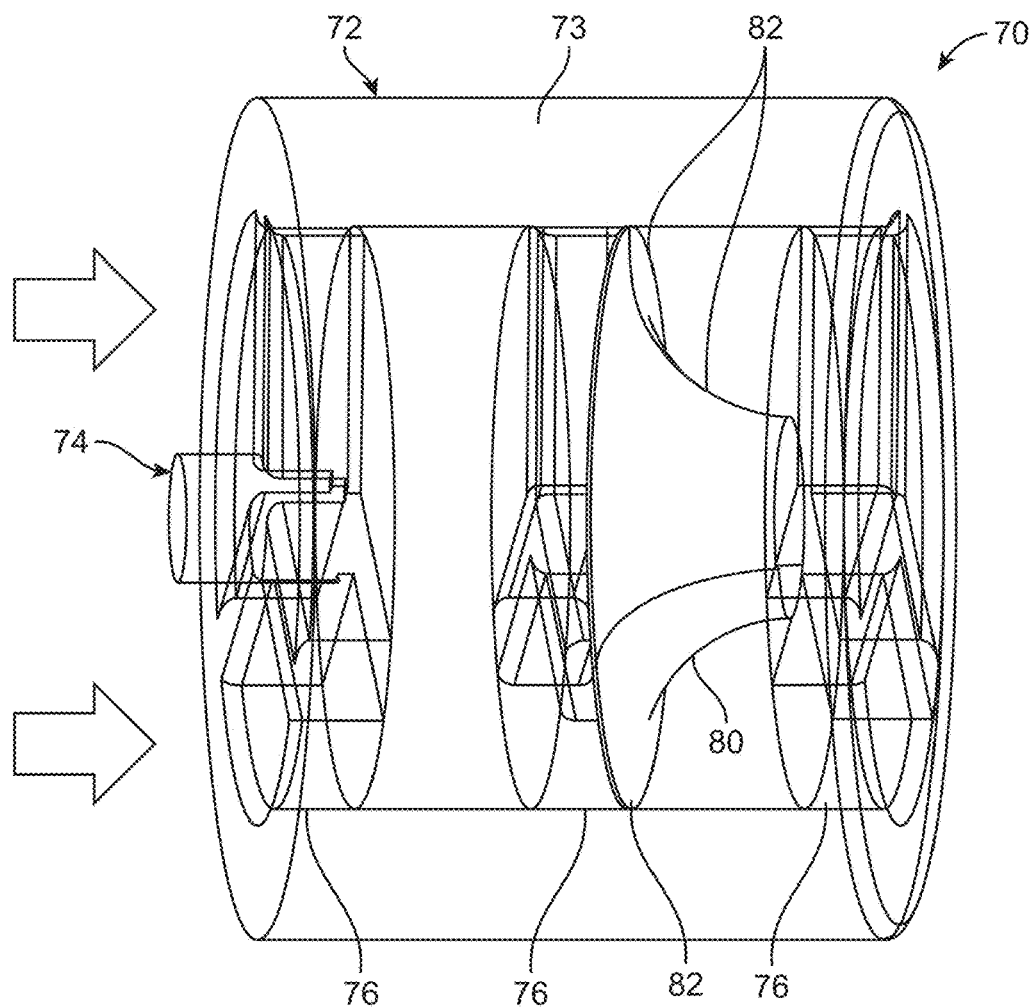
FIG. 5C is a partially transparent side view of the temporary valve of FIGS. 5A-5B.

If the optional temporary prosthetic valve 70 is provided separate from the sizers 38, 40, the temporary prosthetic valve 70 can be of the configuration shown in FIGS. 5A-5D. The temporary prosthetic valve 70 of this embodiment includes a cylindrical wall 72 defining a hollow core 73. The wall 72 can be inflated with fluid or gas via one or more inflation ports 74 that can be fluidly connected to the inflation source (not shown) via the port 68 of the handle assembly 32. For example, the port 68 can be connected to a conduit (not shown) that is routed within the catheter assembly 34, which extends to the port 68 of the handle assembly 32 for connection to the inflation source via the port 68. In this embodiment, the temporary prosthetic valve 70 includes three hollow supports 76 fluidly connected with and extending between the cylindrical wall 72. In one embodiment, the temporary prosthetic valve 70 includes three supports 76 with one support 76 positioned at each end of the temporary prosthetic valve 70 and one support 76 positioned near a middle of the temporary prosthetic valve 70. Each support 76 includes three inflation channels 78 evenly spaced 120 degrees from each other that extend radially from the cylindrical wall 72 to a center axis 75 of the cylindrical wall 72 where the three inflation channels 78 intersect. This arrangement, although not required, provides generally even inflation of the cylindrical wall 72. The cylindrical wall 72 further supports a valve structure 80 having leaflets 82, which become functional once the cylindrical wall 72 is at least partially inflated (e.g., about 60% or more inflated). In other words, upon partial inflation of the cylindrical wall 72, the forward blood flow will push the leaflets 82 open and the leaflets 82 will proceed to function similar to a native heart valve for as long as the cylindrical wall 72 remains at least partially inflated. The inflation channels 78 are configured as to not substantially obstruct blood from through the temporary prosthetic valve 70. The inflation channels 78 can further be configured to provide the leaflets 82 with backward flow resistance. For example, one support 76 can be positioned proximate the leaflets 82 as is best shown in FIG. 5A. The leaflets 82 can be made via dip coating, extrusion or the like and the valve structure 80 can be attached to the cylindrical wall 72 with heat or glue bonding, for example.

Figure 6:
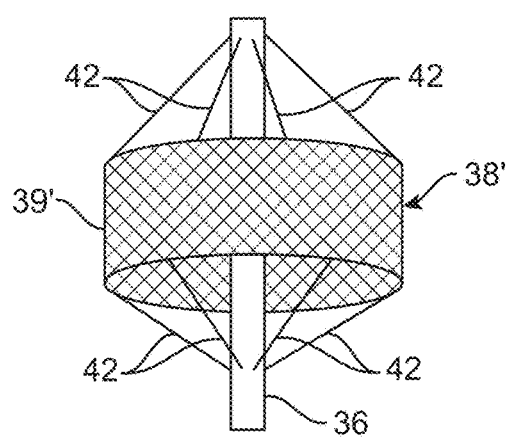
FIG. 6 is a perspective view of an alternate sizer that can be used with the sizing catheter of FIGS. 4A-4B.

The proximal and distal sizers 38, 40 can take a variety of configurations suitable for determining properties of the lumen 10. In some embodiments, as shown in FIG. 6, a sizer 38' can include a ring 39' being an expandable mesh case made of nitinol or other suitable material. The sizer 38' can be actuated and include one or more sensors (not shown) in the same way as disclosed with respect to the sizers 38, 40. In some embodiments, the sizers may be inflatable. For example, each sizer can be a balloon and can include a valve structure including valve leaflets, substantially similar to the temporary prosthetic valve 70, which can be delivered in a deflated, unexpanded position and then inflated via the port 68 of the handle assembly 32 to expand against the respective tissue at a target site. The inflation can be set, for example, to mirror the force that would be applied by a prosthetic heart valve. In some embodiments, the sizers differ in size but are otherwise similarly configured. In other embodiments, the sizers differ both in size and configuration. In other embodiments the sizers and rings can be mechanically actuated devices, such as a ring or a hoop having a diameter that is adjustable. In the disclosed embodiments, the sizers are configured as to generally not obstruct blood flow if the sizers are positioned in a vascular lumen such as an artery or vein, for example.

Referring now also to FIGS. 7A-7E, which illustrate one alternate catheter assembly 134 that can be used with the disclosed sizing catheters, such as the sizing catheter device 34 of FIGS. 4A-4B. In this embodiment, the catheter assembly 134 includes first and second catheters 136a-b as well as proximal and distal sizers 138, 140. The first and second catheters 136a-b are coaxially aligned and sized such that the second catheter 136b is smaller than and fits within the first catheter 136a. In this way, the distance between the proximal and distal sizers 138, 140 can be varied by adjusting the position of the second catheter 136b with respect to the first catheter 136a. In this embodiment, each sizer 138, 140 has both a delivery and a deployed position. The delivery position generally corresponds with delivery of the sizers 138, 140 through the vasculature and the deployed position generally corresponds with the process of obtaining information regarding the lumen of interest. In the delivery position, the respective sizer 138, 140 is positioned within one or more catheters 136a-b. In the deployed or at least partially-deployed position, the respective sizer 138, 140 extends radially outward from at least one of the catheters 136a-b. Each of the sizers 138, 140 may include one or more sensors 146, 148 (schematically shown in FIG. 7A) coupled to or otherwise integrated within the hoop material of the sizer 138, 140 at various points so that they are capable of contacting and obtaining information from adjacent patient tissue. The sensors 146, 148 can be of any of the type disclosed herein and can be evenly spaced around the periphery of the sizer 138, 140 and/or can be provided in a matrix around the sizer 138, 140, as desired.

Figure 7A:
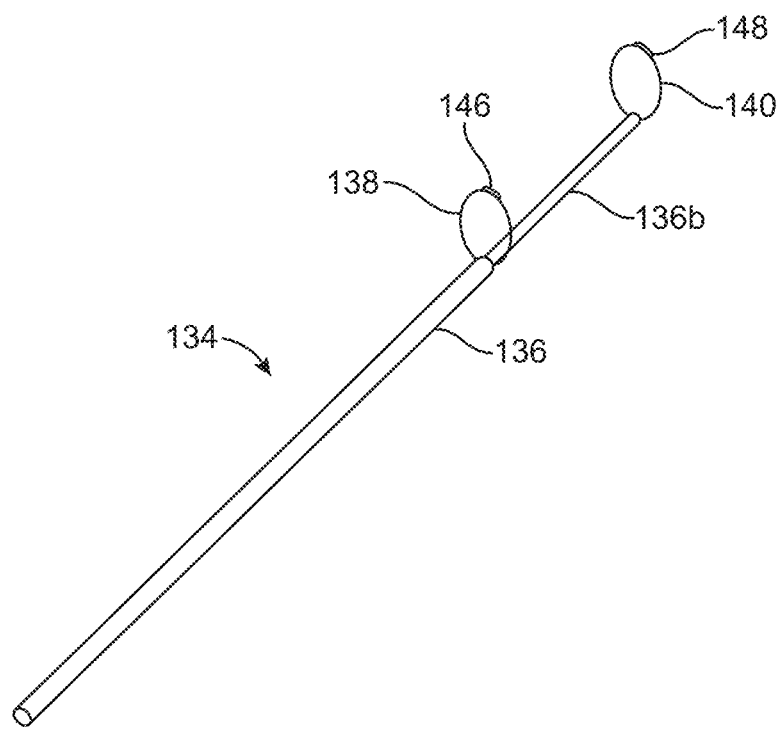
FIG. 7A is a perspective view of an alternate catheter assembly in a delivery configuration that can be used with the sizing catheter of FIGS. 4A-4B.
Figure 7B:
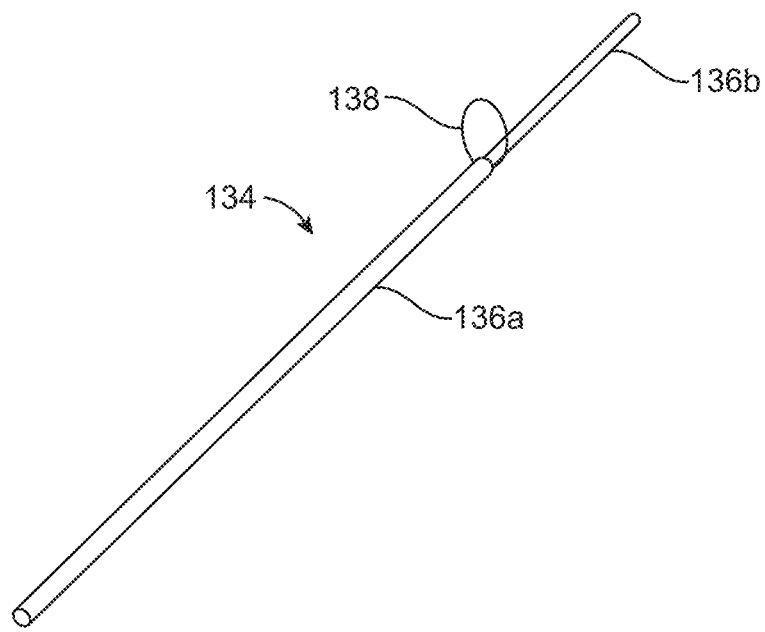
FIG. 7B is a perspective view of the catheter assembly of FIG. 7A in which a proximal sizer is deployed to a first position.
Figure 7C:
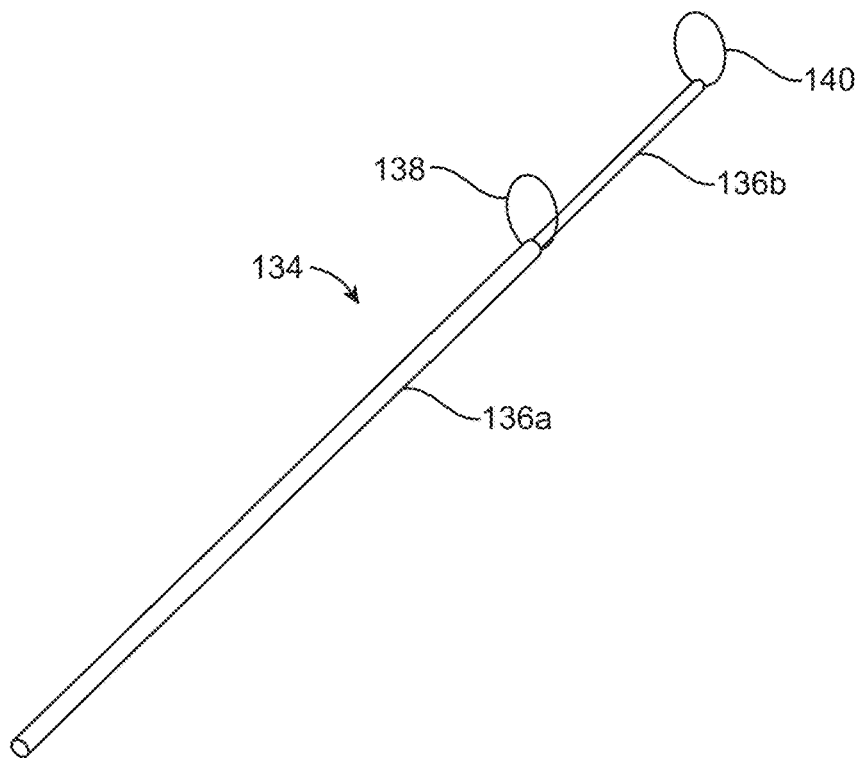
FIG. 7C is a perspective view of the catheter assembly of FIGS. 7A-7B in which a distal sizer is further deployed to a first position.
Figure 7D:
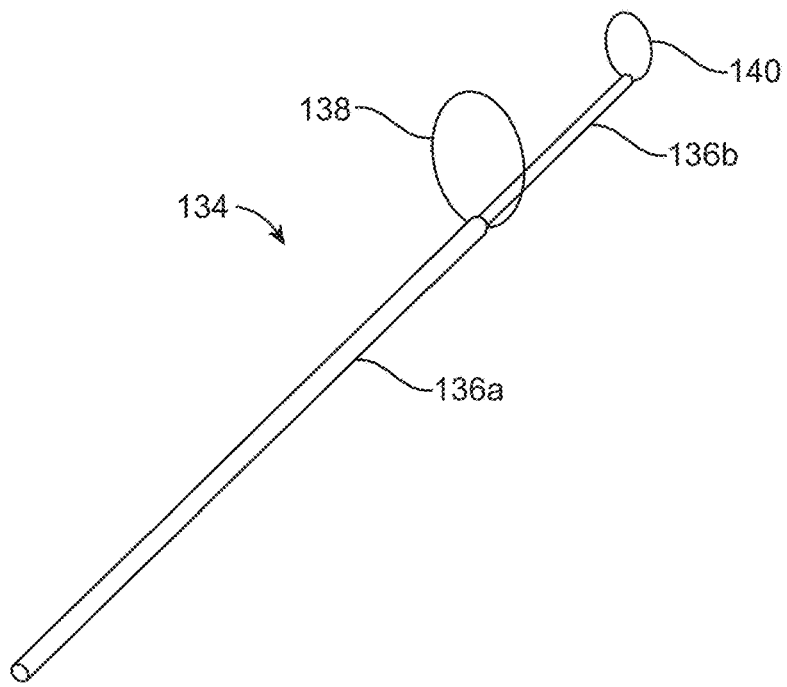
FIG. 7D is a perspective view of the catheter assembly of FIGS. 7A-7C in which the proximal sizer is deployed to a second position.
Figure 7E:
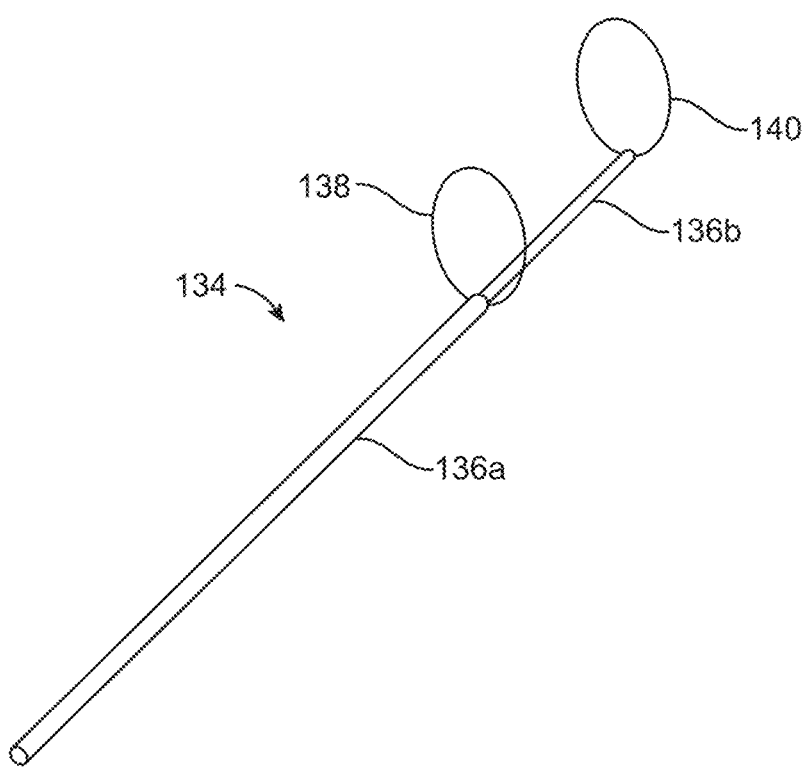
FIG. 7E is a perspective view of the catheter assembly of FIGS. 7A-7D in which the distal sizer is also deployed to a second position.

FIG. 7A illustrates the catheter assembly 134 in a delivery position. FIG. 7B illustrates a proximal sizer 138 of the catheter assembly 134 partially deployed (expanded) and extending radially from the first and second catheters 136a-b at a terminal end of the first catheter 136a. FIG. 7C illustrates the catheter assembly 134 with the proximal sizer 138 partially deployed and the distal sizer 140 extending radially from a distal end of the second catheter 136b and partially deployed (expanded). FIG. 7D illustrates the catheter assembly 134 with the proximal sizer 138 fully deployed (expanded) and the distal sizer 140 partially deployed. FIG. 7E illustrates both sizers 138, 140 being fully deployed.

Figure 8:
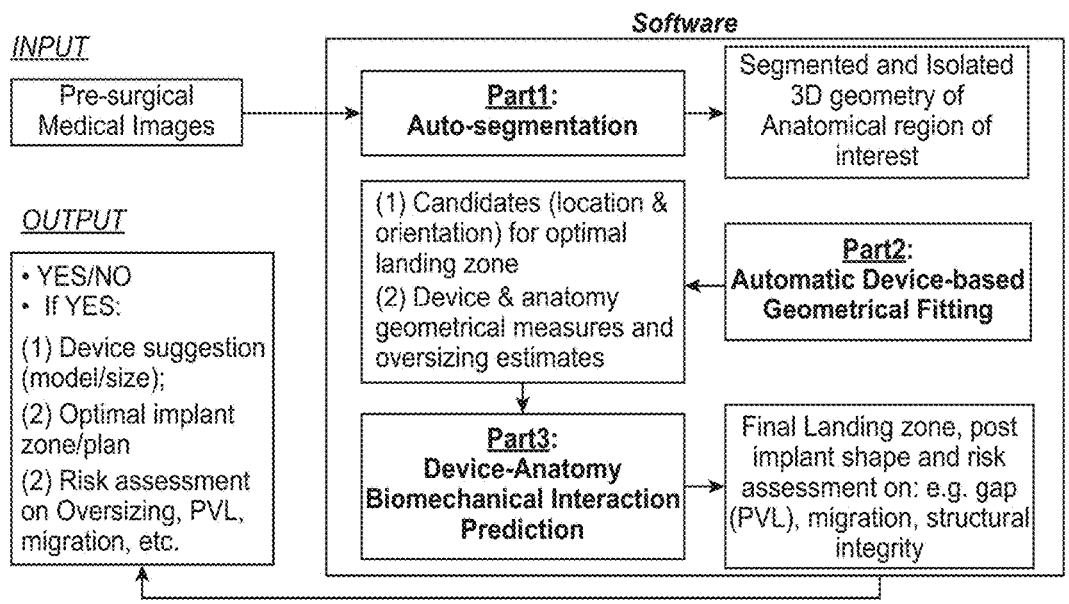
FIG. 8 is a flow diagram of one method of the disclosure.

Additional aspects of the disclosure include methods and software for: 1) automatic patient screening; and/or 2) pre-operative planning of a stented prosthesis ("device") such as any of those disclosed above. Specifically, the method of FIG. 8 begins by obtaining pre-operative images of the anatomy (e.g., a pulmonary artery) in which the stented prosthesis is to be implanted. The images can be obtained from a computed tomography (CT) scan and/or a magnetic resonance (MR) scan or the like, for example. The images are uploaded or otherwise made accessible to a computer operating the software. From that step, the images are collectively auto-segmented using machine-learning (e.g. convolutional neural networks (CNNs)). In this way, the images are automatically segmented using machine-learning techniques (e.g., more specifically deep learning using multiple CNNs). This process outputs 3D segmented volume that is divided into different anatomical structures of interest within the imaging volume (e.g., device landing zone, anatomical structures and landmarks). For example, the CNNs are trained for voxel-wise labeling of cardiac images into structures such as right and left atriums and ventricles as well as ascending aorta and main pulmonary artery. During the auto-segmentation process, bounding boxes are positioned around a target zone of the image. Automatic threshold calculation to identify the anatomy of interest from the background and segmentation of the target zone are conducted in any known manner to achieved desired contrast. In some methods, manual supervision of any or all of the software decisions (e.g., identification of landmarks) is used to confirm accuracy. Alternatively, if physical dimensions of the anatomical structure of interest are known because they were physically measured, for example, with one of the above-referenced devices or the like, the physical measurements can be inputted into the software as an alternative to, or in addition to, uploading images for modeling and device fit testing.

Figure 9A:
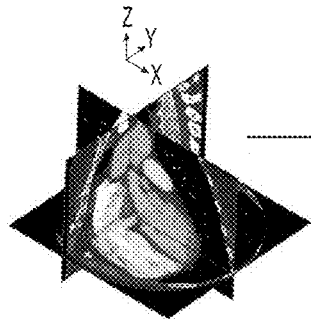
FIG. 9A is a representative example of a 3D image of a patient's anatomy.
Figure 9B:
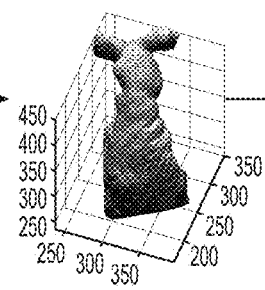
FIG. 9B illustrates an auto-segmented image of FIG. 9A.
Figure 9C:
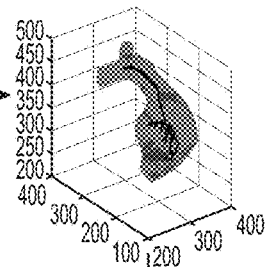
FIG. 9C illustrates the anatomy and a centerline plotted in the auto-segmented image of FIG. 9B.

Next, the software conducts automatic virtual device geometrical fit testing. Particularly, the software conducts an automatic interactive device-based analysis performing device-versus-anatomy geometrical comparison at different device landing scenarios (e.g., variety of device landing zone locations and/or axis orientations). This provides evaluation of factors such as oversizing, gap and fit of one or more devices with respect to the modeled patient anatomy. The software is configured to evaluate a plurality of devices for device position and, also, vectors (i.e. device axis angle). In additional reference to FIG. 9A, the software begins with a three-dimensional image (i.e. the segmented model) of the patient anatomy. With additional reference to FIG. 9B, the software automatically identifies/generates a centerline within an interior of the modeled anatomy. Then, with additional reference to FIG. 9C, the software optionally dilates the centerline. The ratio of dilation is selected with respect to the anatomical size and uncertainty of the centerline calculation. For example, the centerline can be optionally dilated to about 10% of the maximum anatomical lateral size. However, the ratio of dilation may be less or greater, as desired.

Figure 9F:
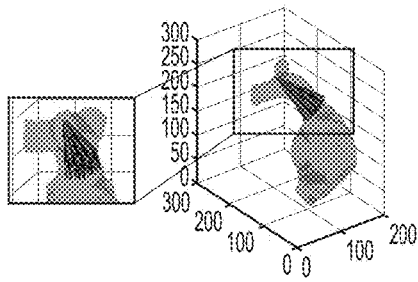
FIG. 9F illustrates a range of device axis orientations.
Figure 9E:
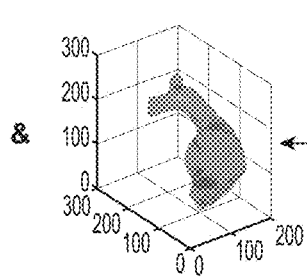
FIG. 9E illustrates a range of prosthesis ("device") positions.
Figure 9D:
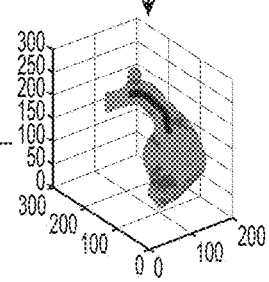
FIG. 9D illustrates the anatomy and centerline of FIG. 9C having been dilated.
Figure 10:
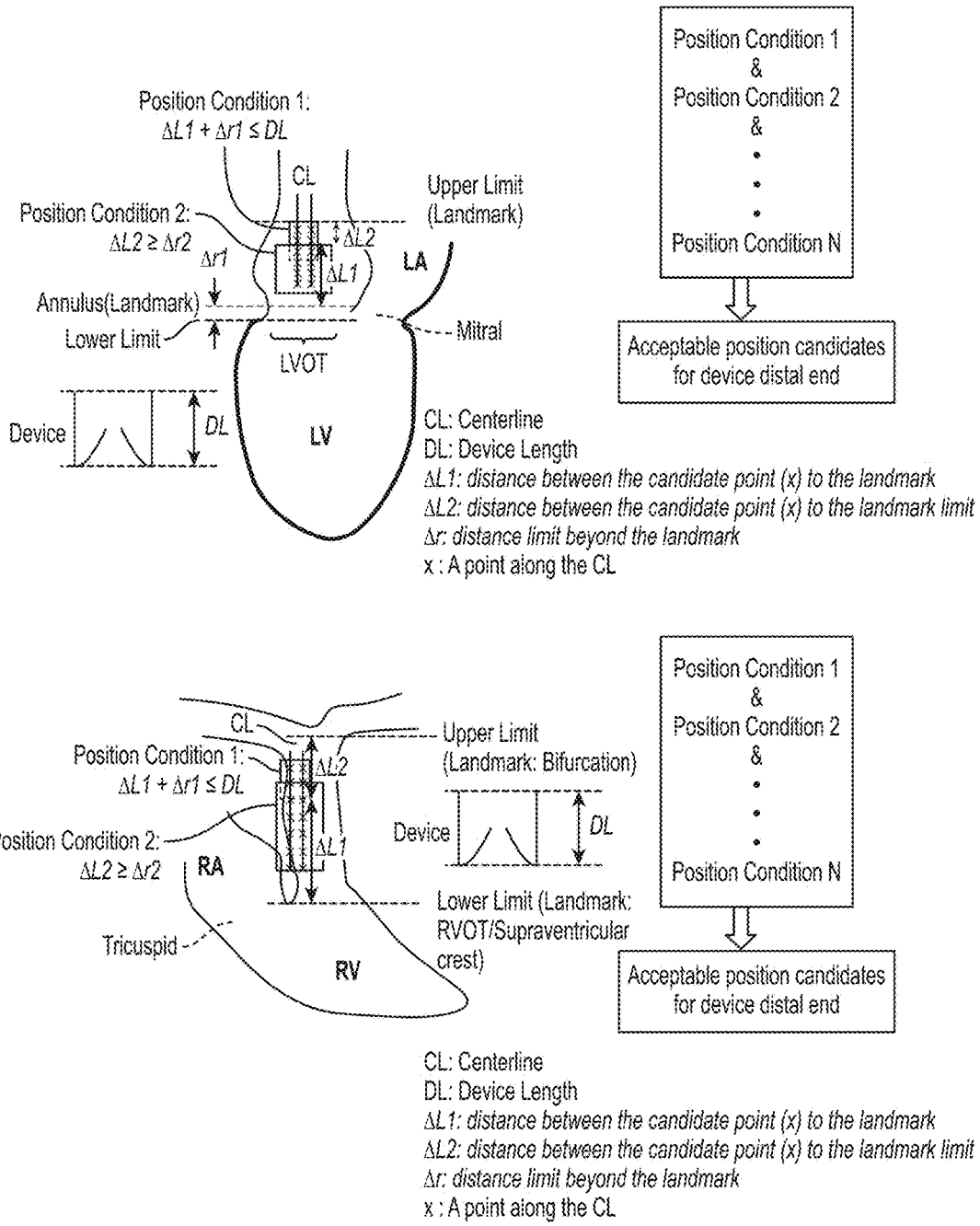
FIG. 10 illustrates various position conditions with respect to the device and anatomy.

With additional reference to FIGS. 9D and 10, the software identifies landing zone or deployment positions of the device upon implantation. This step is conducted using the following data: (1) the geometry of the device (e.g., length DL as shown in FIG. 10); (2) previously identified anatomy landmarks/structures; and (3) the restriction criteria on landing zone, possibly obtained from device instructions for use, (such instructions can include, for example, that the device should not stick into the right ventricle for pulmonary heart valve replacement, the device should not go deeper than a certain length below the annulus for aortic valve replacement (e.g., to prevent the possibility of heart block), the device should not go as high as covering the entire sinuses for aortic valve replacement (e.g., to prevent the possibility of coronary obstruction)). See for example, Aortic Position Condition 1 ($\Delta L1+\Delta r1 \leq DL$) and Aortic Position Condition 2 ($L2 \geq \Delta r2$) of FIG. 10. These potential considerations provide limitations for the software to filter out acceptable position coordinate candidates ("candidate points") from the dilated centerline points CL. The present disclosure is not intended to be limited to any particular combination of considerations. One example of this process and method is outlined for both aortic and pulmonic portions of the anatomy in FIG. 10.

With further reference to FIGS. 9E-9F, the software additionally establishes a range of device axis options. The range of device axis options is calculated by the software from the centerline, a curved centerline experiences a range of tangential vectors (orientation vectors) along its curvature. The software calculates those, and adds a margin (e.g. ±5-10 degrees in 3D) to minimize the effect of centerline calculation uncertainty.

It will be understood that the determinations made in FIGS. 9A-9F can be made concurrently or sequentially in an order that differs from the order of the presented figures. Overall this aspect of the software: (1) takes in a 3D reconstructed geometry (segmented geometry) of the anatomical landing zone (e.g., main pulmonary artery from RVOT to bifurcation for pulmonic valve, from LVOT to arch of the aorta, ascending aorta, for an aortic valve); (2) calculates the centerline of the anatomy and dilates the centerline; (3) identifies the coordinates of location candidates (for a point of reference on the device, e.g. distal end) and device orientation; (4) scores each landing candidate point (a combination of device location and orientation) and comparatively identifies the best. The software, also, optionally provides a manual user interface environment for landing zone evaluations. More specifically, through a graphic user interface (GUI) the user could overlay the device on anatomy in 3D at several desired implant scenarios (locations and axes). The software, then, provides device-based fit score and fit analysis (e.g. perimeter profile of the device versus that of the anatomy) for those manual implanting inputs.

Figure 11A:
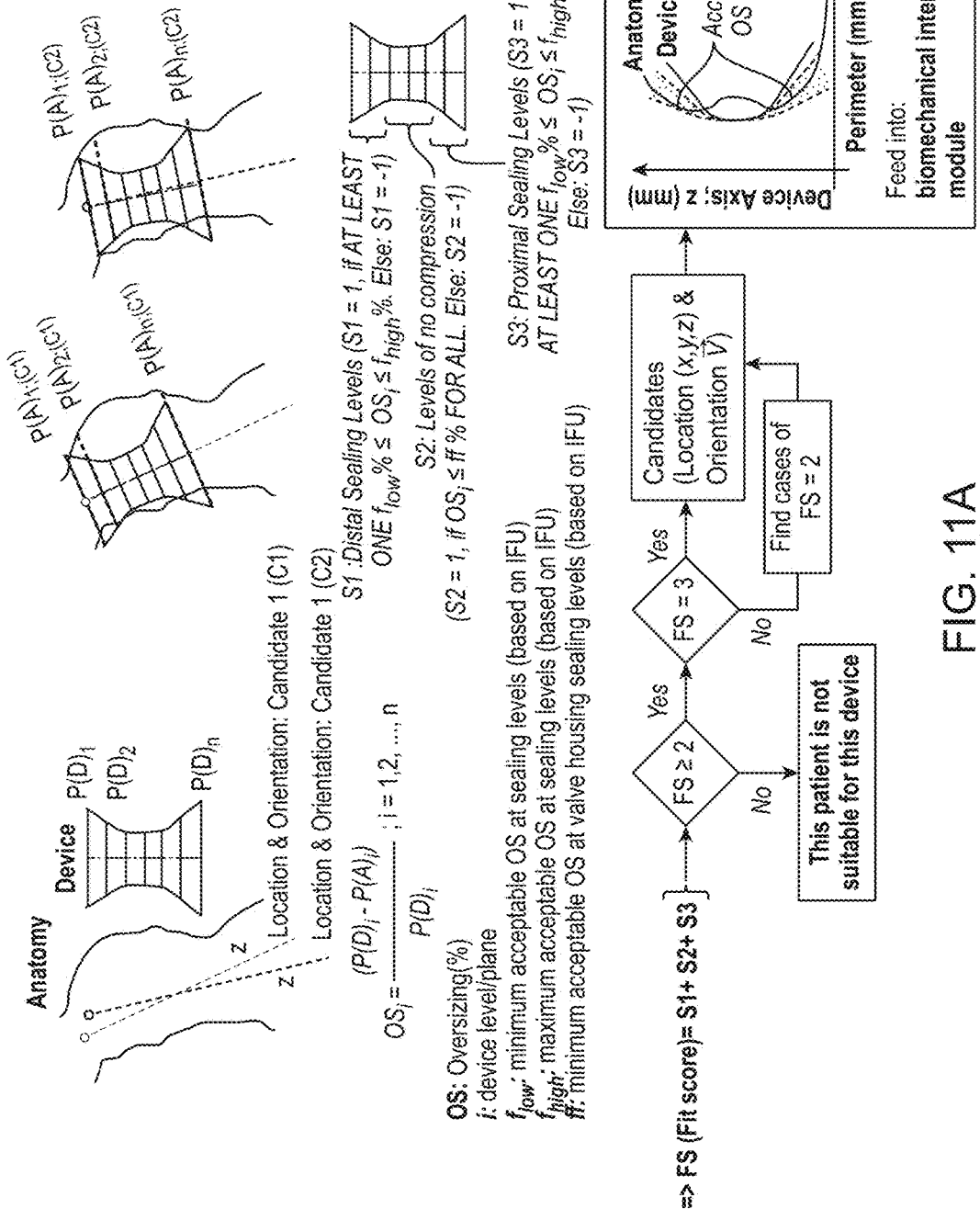
FIGS. 11(a)-11(b) illustrate a determination of fit scores.
Figure 11B:
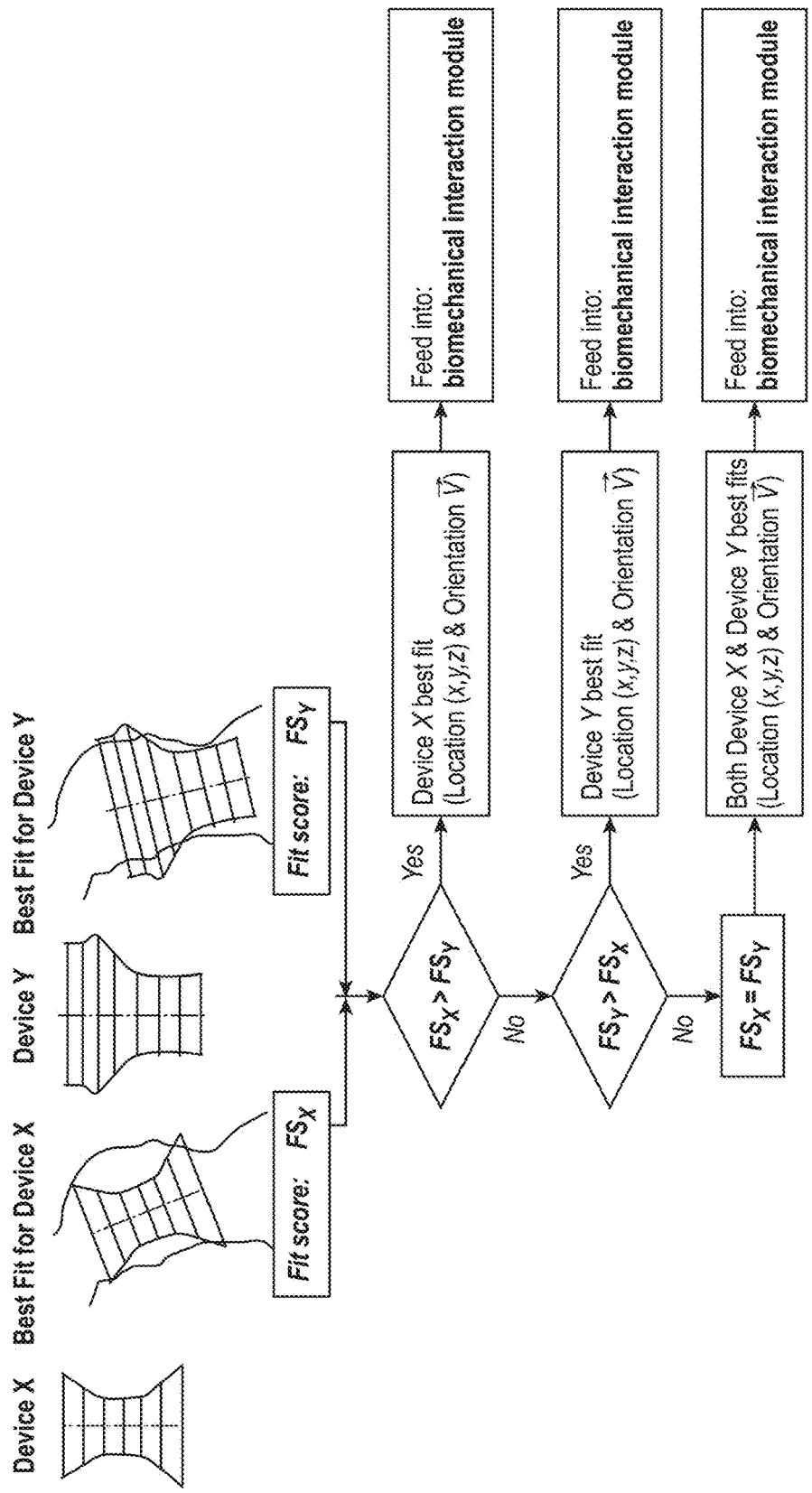

Once potential device landing or deployment positions and device axis orientations are determined, the software is programmed to iteratively compare the implant scenarios for each, or at least a plurality of, potential devices. By analyzing fit criteria as generally outlined in FIG. 11(a) (e.g., perimeter difference, overlap area, geometrical gap and oversizing "OS" ratio (e.g., $$OS_i = \frac{P(D) - P(A)}{P(D)},$$

where P(A) and P(D) represent anatomy and device perimeters on the same plane (i)) at several levels/planes/obliques/slices of device/anatomy or the like) at a plurality of cross-sectioned locations/"segments", the software determines a fit score FS for each device implant scenario. Each "perimeter" P(A) and P(D) represents a maximum width of the anatomy/device at particular locations along a length of the device DL or anatomy, as can generally be seen in FIG. 11(a). Each fit score FS for this illustrative embodiment is the addition of measured sealing levels/locations (e.g. $S_{i=1, 2, 3}$ representing regions of inflow, valve housing, and outflow) along the length of the device DL as virtually implanted. $S_j$ at distal and proximal sealing levels can be programmed to be assigned as follows. $S_j=1$ if at least one $OS_i$ is greater than or equal of $f_{low}\% \leq OS \leq f_{high}\%$ (wherein f % is acceptable oversizing ratio, which is provided in instructions for use ("IFU")/implant protocol of the device use). This ratio should not be higher than certain level to avoid structural failure and should not be below a certain % to avoid risk of migration or paravalvular leakage). If not, $S_j=-1$. For levels of no compression (e.g. valve housing in prosthetic heart valves), $S_j=1$ if $OS \leq ff\%$ (wherein ff % is acceptable oversizing limit, which is provided in instructions for use ("IFU")/implant protocol of the device use) for all; else $S_j=-1$. In the case of a device with three critical levels (i.e. $S_{j=1, 2, 3}$ representing regions of inflow, valve housing, and outflow), if the fit score FS is greater than or equal to 2, the software determines that the device is not suitable for the patient. If the fit score FS is equal to 3, the device is a candidate and will be analyzed by a biomechanical interaction module of the software. Once each implant scenario fit score FS is determined, the fit scores (n represent the number of implant scenarios) FIGS. 11(a)-11(b) are ranked (i.e. compared) to identify one or more of the top scoring (i.e. best) candidates for implant, device position and corresponding device axis. As shown in FIG. 11(b) for purposes of illustration, $FS_x$ is compared to $FS_y$. It will be understood, however, that there is no intended limit to the number of fit scores that can be compared and ranked. In various embodiments, the top scoring candidates will all be analyzed by a biomechanical interaction module of the software.

The biomechanical interaction module is programmed to predict and evaluate the biomechanical interaction between the device and the host anatomy. One main purpose of biomechanical interaction analysis includes providing insights into the interaction between device and specific patient anatomy—preoperatively. Such insights are believed to have tremendous power to accelerate research and development of novel valve-based solutions, as well as ultimately improve clinical outcomes in real-world hospital settings. In addition, another purpose is to more accurately predict the oversizing, optimal landing zone, with respect to migration, paravalvular leakage, etc. Currently, biomechanical interaction is performed through bench testing or computational modeling (e.g. finite element analysis (FEA)). These methods require validation on how well they replicate the real situations. For example, the computational modeling is, specifically, computationally expensive and time consuming. These approaches require user mechanical experimental or modeling expertise, accurate material properties and boundary condition evaluations.

Figure 12:
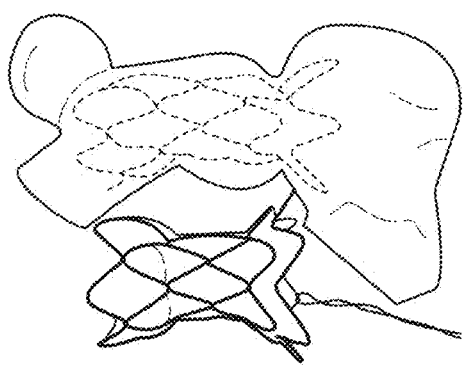
FIG. 12 illustrates an example of one device both pre and post implantation within a patient's anatomy (shown as translucent for clarity).

Biomechanical interaction between an implantable device and patient anatomy is predicted in the present embodiments through a data-driven predictor model of the biomechanical interaction module. The model is a supervised machine learning model that is developed using pre- and post-implant data, provide post implant shape and performance through a real time biomechanical interaction predictor. As is generally illustrated in FIG. 12, a device frequently has one shape pre-implantation (shown on left) that differs substantially from a shape of the device once implanted (shown implanted in a translucent vessel on right) due to competing force exertions between the device and the host vessel anatomy. The biomechanical interaction module is configured to anticipate, or at the very least estimate, the interaction between devices and the host anatomy to inform the physician on oversizing, implanted landing zone, possible paravalvular leakage and so on. This provides important information to avoid improper oversizing, potential migration, and valve leakage and selecting a device that is too long or otherwise in appropriately configured for the particular anatomy upon implantation.

Figure 13A:
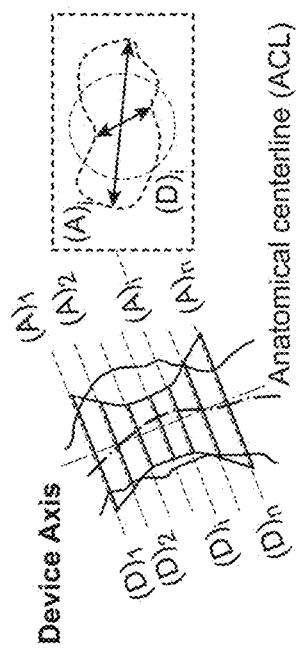
FIGS. 13(a)-13(b) schematically illustrate pre and post implant configurations of both the device and the anatomy, which are predicted and modeled with the software and method of FIG. 8.
Figure 13B:
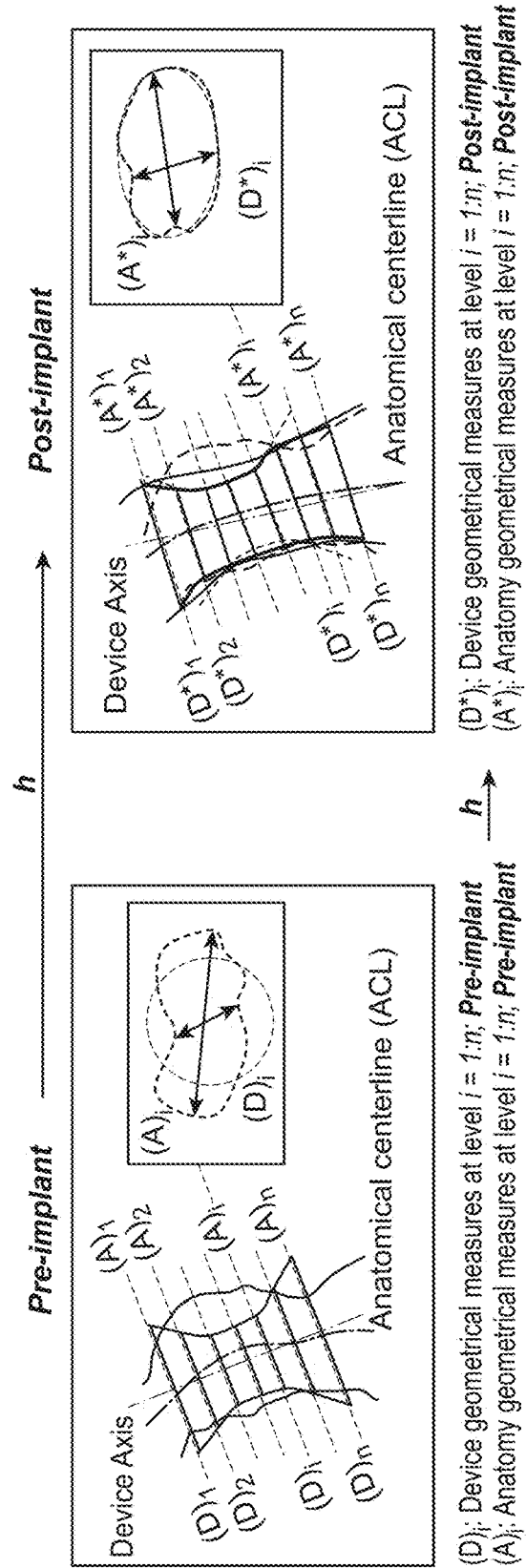

Referring now also to FIGS. 13(a)-13(b), one model for predicting the biomechanical interaction between the device and the host anatomy (compliance and deformation) is summarized as follows: h (D,A↔D*,A*). $D_i$ and $A_i$ represent device and anatomy geometrical parameters/factors/identifiers (including, but not limited to, cross-sectional maximum and minimum diameters, cross-sectional perimeter derive diameter, cross-sectional area, curvature, cross-sectional ellipticity, and etc.), at device i respectively. Notably, $D^*_i$ and $A^*_i$ represent the corresponding post-implant pairs. In this approach or technique: first the device and anatomy geometries are parameterized into defining parameters for landing zone candidates (estimated in the last step (FIG. 13(a)). The defining parameters are characterized at several levels along a length of the device (FIG. 13(a)), and include factors (such as cross-sectional maximum and minimum diameters, cross-sectional perimeter derive diameter, cross-sectional area, curvature, cross-sectional ellipticity, and etc.) that are measured for anatomy on device based planes of a landing zone candidate for critical phases, or all phases, of the cardiac cycle (e.g. systole and diastole, this depends on device instructions for use and characterization/screening protocol). The transfer function, h (FIG. 13(b)), (or as called in machine learning: hypothesis) then predicts corresponding parameters of post-implant space.

The biomechanical interaction predictive model ,i.e. h, is formed from using a supervised machine learning approach or technique trained with existing datasets that include both pre- and post-implant. Specifically, the parameterized pre- and post-implant datasets are used for training the algorithm. The trained model, then, is capable of mapping the pre-implant parameters of a new patient to those of the post-implant. Modeling begins with identifying anatomy and device geometrical parameters at various points/levels along a length of the device, and slightly beyond it (e.g., 10% of device length on both proximal and distal ends of the device), to be implanted (FIG. 13(a)). At this stage, i.e. FIG. 13(b) "pre-implant", no account is made for the biomechanical interaction between the device and the anatomy. Therefore, it is likely that if the device is implanted in the modeled anatomy, the final result will not resemble what is illustrated. FIG. 13(b) "post-implant" illustrates an example of how both the device and the modeled anatomy are predicted to generally look given biomechanical interaction between the device and the anatomy (i.e. $D^*_1$-$D^*_n$; $A^*_1$-$A^*_n$).

Various models can be prepared for determining the biomechanical interaction between the implanted device and the anatomy ($D'_1$-$D'_n$; $A^*_1$-$A^*_n$). In one simplified example, FEA can be implemented for each patient. Alternatively, machine learning can be incorporated using existing pre versus post implant CT/MR imaging data that is collected and entered into the software. In this software, the computational modeling and experimentations (e.g. FEA, animal model, cadaver studies, and bench testing) are used to extend the number of dataset with both pre- and post-implant. For example, FEA is used to extend pre to post prediction to those in which only pre-implantation data is available. It is noted that the number of cases to span the space when FEA is used to extend pre to post implantation prediction to those with only pre-implantation data are selected to represent the patient population, e.g. both extreme and average geometrical features that could be identified using geometrical model analysis (e.g., statistical shape modeling "SSM"). modal analysis (e.g., statistical shape modeling "SSM"). Finally the training dataset, representing the target population, could include one or both of the following categories: (1) in-vivo/in-vitro measurements (pre and post implant CT/MR images); and (2) computationally modeled cases (on both patient-specific anatomies, or virtually generated anatomies).

After modeling all implant scenarios post implantation (i.e. given the predicted biomechanical interaction using trained model, i.e. h) the implant scenarios are scored and ranked. The software then outputs recommendations on, device (model/size) as well as a suggested optimal position or zone for implantation including an implant position and device axis orientation. As desired and based on the results of the analysis conducted by the software, more than one device may be recommended. In addition, the software provides assessments on post-implant risks (e.g. paravalvular leak (PVL), structural failure, device migration and etc.) through biomechanical predictive model.

In view of the above, one embodiment of the present disclosure includes a method of deploying a prosthesis or device (e.g., a heart valve prosthesis) within a lumen of a patient's anatomy (e.g., a pulmonary artery). The method comprises the delivery of a distal portion of a lumen sizing catheter device, such as any of those disclosed above, to a target site within the lumen. As described above with respect to various embodiments, the lumen sizing catheter device includes a handle assembly, a catheter extending from the handle assembly, a distal portion comprising a distal sizer positioned on the catheter proximal a distal end of the catheter, and a proximal sizer positioned on the catheter and spaced proximally from the distal sizer. The proximal and distal sizers are delivered to the target site within the lumen. The proximal and distal sizers are used to determine a first lumen dimension proximate the distal sizer and a second lumen dimension proximate the proximal sizer. In addition, the distance between the distal and proximal sizers is determined. Based on the first and second lumen dimensions as well as the distance between the sizers is used to create a three-dimensional model of the target site of the lumen as also described above. Based on the three-dimensional model, a plurality of potential prosthesis deployment positions and axis orientations relative to the lumen is determined. A geometric fit analysis is then performed by iteratively comparing the geometry of a plurality of differently sized prostheses to the plurality of potential prosthesis deployment positions and axis orientations to thereby identify one or more appropriately sized prostheses based on one or more geometric fit parameters (as discussed above). A biomechanical interaction analysis is then performed in the manner disclosed above between the one or more appropriately sized prostheses and the patient's anatomy to select a properly sized prosthesis for implantation within the lumen. The properly sized prosthesis is then implanted or deployed within the lumen. In various embodiments, the proximal sizer is adjustably spaced from the distal sizer (e.g., see the embodiment of FIGS. 7A-7E and related disclosure). In various embodiments, the distal and proximal sizers are configured to determine first and second dimensions of the lumen at a selected distance between the distal and proximal sizers (e.g., see the embodiment of FIGS. 7A-7E and related disclosure). In various embodiments, the distal and/or proximal sizers include a hoop having an adjustable diameter (e.g., see the embodiment of FIGS. 7A-7E and related disclosure). In various embodiments, in a deployed position, the distal sizer and the proximal sizer are different sizes (e.g., see the embodiments of FIGS. 4B and 7D and related disclosure). In various disclosed embodiments, the distal sizer is spaced from the proximal sizer between about 5 and about 100 mm. In various embodiments, the distal and/or proximal sizers are inflatable. In various embodiments, the distal and/or proximal sizers are adjustable in diameter via the handle assembly (e.g., see the embodiments of FIGS. 4B and 7D and related disclosure). In various embodiments, the distance between the sizers is adjustable independent of adjustment of a diameter of the proximal or distal sizer (e.g., see the embodiments of FIGS. 4A and 7A and related disclosure). In various embodiments, the distal and/or proximal sizers include a valve structure as discussed above. In various embodiments, the distal and proximal sizers include a lumen to allow for blood flow through the distal and proximal sizers (e.g., see the embodiments of FIGS. 4A and 7A and related disclosure). In various embodiments, the lumen sizing catheter device further comprises a prosthetic valve positioned on the catheter between the distal sizer and the proximal sizer as discussed above. In various embodiments as described above, at least one of the proximal and distal sizers includes a sensor selected from the group consisting of a mechanical sensor and an impedance sensor. In various embodiments, the proximal sizer is adjustably spaced from the distal sizer as described above. In various embodiments as described above with respect to FIGS. 8-13(b), CT or MR imaging data of a portion of the patient's anatomy including the lumen can be used to create or help create a three-dimensional model of the patient's anatomy including the lumen. In various embodiments, the three-dimensional model of the target site of the lumen includes the use of images from one or more imaging techniques of the patient's anatomy as described above. In various embodiments, one or more data-driven machine learning techniques can be used in one or more analyses as described above with respect to FIGS. 8-13(b). In various embodiments, FEA can be used in one or more analyses as disclosed with respect to FIGS. 8-13(b). In various embodiments, statistical shape modeling can be used in one or more analyses as disclosed with respect to FIGS. 8-13(b). In various embodiments, an optimal prosthesis or device deployment position and axis orientation within the lumen is determined as described above. In various embodiments, a prosthesis is selected for implantation or deployment within the lumen in an optimal position and axis orientation as determined by one or more analyses described above with respect to FIGS. 8-13(b).

Although the embodiments disclosed above are most frequently discussed in the context of assessing the parameters of a pulmonary artery, it is to be understood that the embodiments disclosed herein can be applied to devices for sizing other bodily lumens or orifices.

Although the present disclosure has been described with reference to preferred embodiments, workers skilled in the art will recognize that changes can be made in form and detail without departing from the spirit and scope of the present disclosure.

What is claimed is:
1. A method of selecting a prosthesis for implantation within a lumen of a patient's anatomy comprising:
  providing a lumen sizing device comprising:
    a handle assembly,
    a catheter extending from the handle assembly,
    a distal sizer positioned on the catheter proximal a distal end of the catheter, and
    a proximal sizer positioned on the catheter and spaced proximally from the distal sizer;
  delivering the proximal and distal sizers to a target site within the lumen;
  determining a first lumen dimension proximate the distal sizer, determining a second lumen dimension proximate the proximal sizer, and determining a distance between the distal and proximal sizers;
  creating a three-dimensional model of the target site of the lumen based on a diameter of the first lumen, a diameter of the second lumen, and the distance between the first and second lumen diameters;
  determining a plurality of potential prosthesis deployment positions and axis orientations relative to the three-dimensional model;
  conducting a geometric fit analysis by iteratively comparing the geometry of a plurality of differently sized prostheses to the plurality of potential prosthesis deployment positions and axis orientations to identify one or more appropriately sized prostheses based on one or more geometric fit parameters; and
  conducting a biomechanical interaction analysis between the one or more appropriately sized prostheses and the patient's anatomy to select a prosthesis for implantation.

2. The method of claim 1, wherein the proximal sizer is adjustably spaced from the distal sizer.

3. The method of claim 2, wherein the distal and proximal sizers are configured to determine first and second dimensions of the lumen at a selected distance between the distal and proximal sizers.

4. The method of claim 1, wherein the distal or proximal sizer includes a hoop having an adjustable diameter.

5. The method of claim 1, wherein, in a deployed position, the distal sizer and the proximal sizer are different sizes.

6. The method of claim 1, wherein the distal sizer is spaced from the proximal sizer between about 5 and about 100 mm.

7. The method of claim 1, wherein the distal or proximal sizers are inflatable.

8. The method of claim 1, wherein the distal or proximal sizer is adjustable in diameter via the handle assembly.

9. The method of claim 8, wherein the distance between the sizers is adjustable independent of adjustment of a diameter of the proximal or distal sizer.

10. The method of claim 1, wherein the distal or proximal sizer includes a valve structure.

11. The method of claim 1, wherein the distal and proximal sizers include a lumen to allow for blood flow through the distal and proximal sizers.

12. The method of claim 1, wherein the lumen sizing device further comprises a prosthetic valve positioned on the catheter between the distal sizer and the proximal sizer.

13. The method of claim 1, wherein at least one of the proximal and distal sizers includes a sensor selected from the group consisting of a mechanical sensor and an impedance sensor.

14. The method of claim 1, wherein the proximal sizer is adjustably spaced from the distal sizer and further comprising adjusting the distance between the sizers.

15. The method of claim 1, further comprising the step of CT or MR imaging of a portion of the patient's anatomy including the lumen.

16. The method of claim 15, wherein creating the three-dimensional model of the target site of the lumen includes the use of images from the step of imaging of the patient's anatomy.

17. The method of claim 1, further comprises one or more data-driven machine learning techniques.

18. The method of claim 1, further comprises FEA.

19. The method of claim 1, further comprises statistical shape modeling.

20. The method of claim 1, further comprising the step of determining an optimal prosthesis deployment position and axis orientation and further comprising the step of deploying the selected prosthesis within the lumen in the optimal position and axis orientation.

* * * * *